United States Patent
Klitmose et al.

(10) Patent No.: US 6,474,219 B2
(45) Date of Patent: Nov. 5, 2002

(54) FLEXIBLE PISTON ROD

(75) Inventors: Lars Peter Klitmose, Gentofte (DK); Henrik Ljunggreen, Ballerup (DK)

(73) Assignee: Novo Nordisk A/S, Bagsvaerd (DK)

( * ) Notice: Subject to any disclaimer, the term of this patent is extended or adjusted under 35 U.S.C. 154(b) by 20 days.

(21) Appl. No.: 09/808,497

(22) Filed: Mar. 14, 2001

(65) Prior Publication Data

US 2001/0023637 A1 Sep. 27, 2001

Related U.S. Application Data

(60) Provisional application No. 60/193,756, filed on Mar. 31, 2000.

(30) Foreign Application Priority Data

Mar. 24, 2000 (DK) .................................. PA 2000 00496

(51) Int. Cl.[7] .................................................. F01B 9/00
(52) U.S. Cl. ......................................... 92/137; 604/224
(58) Field of Search ................... 92/136, 137; 604/214, 604/224, 228

(56) References Cited

U.S. PATENT DOCUMENTS

| 1,608,275 A | 11/1926 | Grier et al. |
| 4,318,499 A | 3/1982 | Hamilton |
| 4,493,704 A | 1/1985 | Beard et al. |
| 5,261,882 A | 11/1993 | Sealfon |
| 5,957,889 A | * 9/1999 | Poulsen et al. ............ 604/218 |
| 6,003,736 A | 12/1999 | Ljunggren |
| 6,045,537 A | 4/2000 | Klitmose |

FOREIGN PATENT DOCUMENTS

| GB | 33 31 424 A1 | 8/1983 |
| GB | 2145795 A | * 4/1985 |
| WO | WO 84/01109 | 9/1983 |
| WO | WO 95/09021 | 9/1994 |
| WO | WO 98/01173 | 6/1997 |
| WO | WO 98/57688 | 6/1998 |
| WO | WO 99/22788 | 10/1998 |

* cited by examiner

*Primary Examiner*—Edward K. Look
*Assistant Examiner*—Thomas E. Lazo
(74) *Attorney, Agent, or Firm*—Marc A Began, Esq.; Richard Bork, Esq.; Reza Green

(57) ABSTRACT

A flexible piston rod for an injection device, which piston has the form of a helical spring made from a number of narrowly adjacent turns of windings. These turns provide an external thread fitting into the internal thread of a nut element. When the nut element is rotated, the piston rod is advanced forward, which movement is used to displace a piston inside a cartridge containing a fluid to be expelled. In order to prevent the piston rod from rotating when the nut element is rotated, the helical spring making up the piston rod is provided with a longitudinal spine, which is located at a peripheral area of the helical spring.

9 Claims, 2 Drawing Sheets

FLEXIBLE PISTON ROD

CROSS-REFERENCE TO RELATED APPLICATIONS

This application claims priority under 35 U.S.C. 119 of Danish application no. 60/193,756 filed Mar. 31, 2000 and Danish application no. PA 2000 00496 dated Mar. 24, 2000, the contents of which are fully incorporated herein by reference.

The invention relates to a flexible piston rod for an injection device, which piston rod has the form of a helical spring for moving a piston forward inside a cartridge containing a liquid. The flexible piston rod transmits a movement from a piston rod drive to a longitudinal displacement of the piston; the flexible piston rod has a distal end abutting to the piston inside the cartridge, and a proximal end being deflected away from the axis of the cartridge. The piston rod drive drives the flexible piston rod and comprises of a rotating nut element engaging the flexible piston rod.

Such flexible rods are E.g. used in the new generation of very short injection devices for distributing medicine into the body. Some medication, such as insulin, is often self-administered. The typical diabetes patients will require injections of insulin several times during the course of the day. The amount of doses, and the size of each dose is usually prescribed for the individual patient, and it is a key issue for the health condition of the patients that the injection device is able to administer a very precise dose WO 95/09021 shows a displacement system for controlled infusion of a liquid. The flexible piston rod shown has in a preferred embodiment the form of a helical spring with narrowly adjacent turns of windings, which windings provides an external thread. A piston rod drive is provided, which transmit a drive force to the piston through a nut element having an internal thread engaging the external thread of the flexible rod. By rotating the nut element, which is locked for axial movement, the flexible piston rod will drive the piston forward inside the cartridge.

The relationship between the revolutions of the nut element and the piston advancement has to be very precise in order to deliver the correct dose of liquid through the outlet of the cartridge. With the displacement system described above, the flexible piston rod has a tendency to rotate when the nut is rotated making the displacement of the piston somewhat uncontrolable.

It is an object of the invention to provide a flexible piston rod of the above mentioned type, which will remain non rotational when the nut element of the piston rod drive is rotated, making the relation between the revolutions of the nut element and the advancement of the piston of a constant size.

This is obtained by a flexible piston rod, having the form of a helical spring made up from a number of narrowly adjacent turns of windings providing an external thread, for moving a piston forward inside a cartridge containing a liquid, said flexible piston rod transmitting a movement from a piston rod drive to a longitudinal displacement of said piston, said flexible piston rod having a distal part abutting said piston inside said cartridge and a proximal part being deflected away from the axis of said cartridge, said piston rod drive including a nut element having an internal thread engaging said external thread of said flexible piston rod and which nut element is locked against longitudinal displacement and forcedly rotated, Which flexible piston rod is characterized in that said flexible piston rod has means locking said flexible piston rod against rotation.

The nut element has an internal thread corresponding to the external thread on the flexible piston rod. With the nut element locked against axial displacement, the rotation of the nut will advance the flexible piston rod moving the piston forward inside the cartridge. To rotate the nut element a large variety of different mechanical solutions can be used. A solution where an injection button worked by the fingers of the user drives the nut element would be very useful. It is however found most useful to use an electric motor, which through a suitable gearing can rotate the nut element.

In order to prevent the flexible piston rod from rotating when the nut element is rotated it is necessary to lock the flexible piston rod against rotation. This can according to the invention be done by guiding a protrusion on the spring in a longitudinal slot, which slot could be placed in the curved guiding path, or by making the spring noncircular and fitting the spring through a non circular guiding element.

In one preferred embodiment of the flexible piston rod according to the invention the means locking the flexible piston rod against rotation is a longitudinal spine situated at the peripheral area of the helical spring forming the flexible piston rod. If the flexible piston rod forming a helical spring has such a spine, the rod will tend to fall into a predetermined position when ever bended. If the helical spring is deflected to follow an arc of a circle, the predetermined position will be one where the spine is situated on the inwardly pointing peripheral side of the bended spring. When rotating the nut element, the flexible piston rod will remain locked in this position, and the relation between the revolutions of the nut element and the advancement of the piston will be of a constant size depending purely on the pitch of the thread connection.

In another embodiment of the flexible rod according to the invention the helical spring has an initial tension and the spine is a removal or a reduction of the initial tension in a longitudinal area of the helical spring. Removing or reducing the build-in initial tension of the helical spring forming the flexible piston rod can introduce a displaced spine into the spring without physically changing the circular appearance of the spring. The initial tension is removed or reduced in a limited angular area of each winding, which areas together forms a straight longitudinal spinal area.

In yet another embodiment of the flexible piston rod according to the invention the spine is a depression in the out-turned peripheral area of each winding covering an angular part being substantial smaller than 360 degrees. This depression making the spring non-circular is according to an appropriate embodiment of the invention introduced into the spring by applying a momentarily force or a pressure over an area on the out-turned peripheral area each winding.

In yet a preferred embodiment of the flexible piston rod according to the invention the momentarily force or the pressure is applied by forcing said flexible piston rod over a relatively sharp edge. This forced a part of the pre-stressed windings back into a non-stressed position, thereby introducing a dislocated spine into the spring.

In another embodiment of the flexible piston rod according to the invention the spine is introduced into the helical spring by physical removing a part of the out-turned peripheral area of each winding covering an angular part being substantial smaller than 360 degrees. The removing of the material forming the part of the spring to be removed is in a preferred embodiment of the flexible piston rod according to the invention done by grinding. By grinding a part of each winding of the helical spring away, the spring is given a noncircular appearance, with the chord of each winding together forming the longitudinal spine.

In a last embodiment of the flexible piston rod according to the invention the spine is introduced into the helical spring when the spring is being coiled. When manufacturing a spring the windings are being coiled into a circular shape. If however they windings, and the spring, is given a different shape, a displaced spine can be introduced into the helical spring at this point.

The invention will be explained more fully below in connection with a preferred embodiment and with reference to the drawing in which:

FIG. 1 Schematically shows a displacement system having a flexible piston rod according to the invention.

The figures are schematic and simplified for clarity, and they just show details, which are essential to the understanding of the invention, while other details are left out. Throughout, the same reference numerals are used for identical or corresponding parts.

For the purposes of the description of the present invention, the term "distal end" of the piston rod 4 is meant to refer to the end abutting the piston 3, whereas the term "proximal end" is meant to refer to the opposite end.

Figure 1:
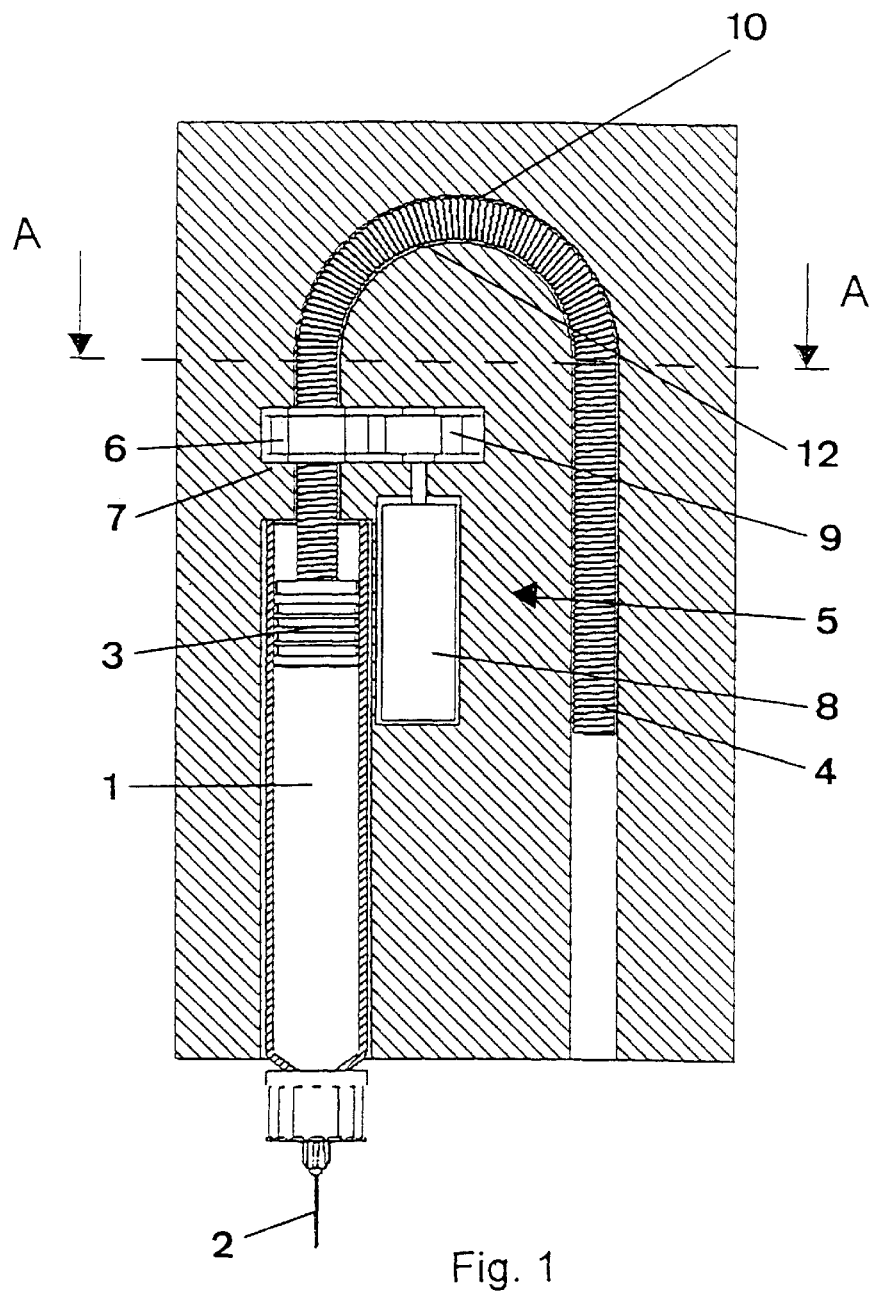

FIG. 1 shows schematically a displacement system for controlled infusion of a liquid. A cartridge 1 is at one end closed by a closure enabling the mounting of a needle or a catheter 2, which needle or catheter 2 is connected with a liquid medicine in the cartridge 1. At its other end the cartridge 1 is closed by a piston 3, which by a flexible piston rod 4 may be pressed into the cartridge 1 to press out the liquid medicine through the needle or catheter 2. The distal end of the flexible piston rod 4 abuts the piston 3, while the proximal end of the flexible piston rod 4 is deflected away from the axis of the cartridge 1. A piston washer can be provided between the piston 3 and the piston rod 4.

The flexible piston rod 4 is made as a helical spring having a number of narrowly adjacent turns of windings abutting each other, which windings provide an external thread.

An ordinary helical compression spring 4 applies a constant force when the two ends of the spring 4 are pulled away from each other. When such a spring 4 is at rest i.e. no pulling is being executed, the force delivered by the spring 4 is normally zero. Helical compression springs 4 can however be produced with an initial tension. Springs of this type are often referred to as extension springs. By coiling one winding backwards and partly over the neighbouring winding when manufacturing the spring 4, the spring 4 will be provided with a build-in initial tension. The backward pointing winding of the windings most be performed in a way keeping a constant diameter of the wound helix, therefore the initial tension, measured as the load needed to overcome the internal force and start coil separation, is generally designed as a few percent of maximum shear stress.

When a spring 4 with initial tension is at rest i.e. no pulling is being executed, the force delivered by the spring 4 will be above zero. A certain pulling force is needed before the windings of the spring 4 start to separate.

The piston drive 5 is made up from a nut element 6, which is locked against axial displacement by a shoulder 7 in a not shown housing. This nut element 6 has an internal thread engaging the external thread of the flexible piston rod 4. The nut element 6 is rotated by an electric motor 8 through a gearing wheel 9. The cartridge 1 and the piston drive 5 are mounted in a not shown housing so that they may not be displaced in relation to each other.

The flexible piston rod 4 is deflected away from the axis of the cartridge 1. If the angle of deflection is 180 degrees the proximal part of the flexible piston rod is parallel with the distal part of the flexible piston rod. In this way the injection device can be made very short and very compact. The bended part of the flexible piston rod, being the part between the distal part and the proximal part, can be guided along a curved path 10.

However it is not necessary to guide the bended part. The helical spring 4 can contain a stiff wire, which is bended into the shape wanted, or the proximal part of the helical spring 4 can be provided with yet another not shown nut element secured in the housing against longitudinal displacement. If so wanted this second nut element can be driven by the same piston rod drive that drives the first nut element.

Now when rotating the nut element 6 the flexible piston rod 4 will advance and move the piston 3 forward inside the cartridge 1, and thereby press the liquid contained in the cartridge out through the needle or catheter 2.

However when rotating the nut element 6, the flexible piston rod 4 tends to rotate due to the friction between the threads connecting the nut member 6 and the flexible piston rod 4. To keep a controlled deliverance of liquid flowing from the cartridge 1 it is important to avoid this rotation of the flexible piston rod 4.

Such a rotation can be prevented by guiding an abutment on the spring 4 in a passage in the housing or in the curved path 10. Another way of preventing the rotation is by introducing a spine 11 into the flexible piston rod 4. With a longitudinal spine 11 inserted in the peripheral side of the spring 4, this spring will always situate itself, whenever bended, with the spine being situated on the inwardly pointing part 12 of the bended spring 4, and at the same time the spine 11 will prevent the flexible piston rod 4 from rotating when a rotating force is being applied to the flexible piston rod 4.

Figure 2:
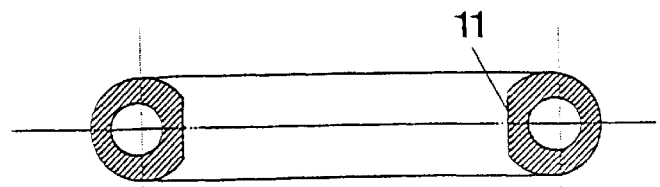
FIG. 2 Shows a sectional view of the flexible piston rod along the line AA in FIG. 1.
Figure 3:
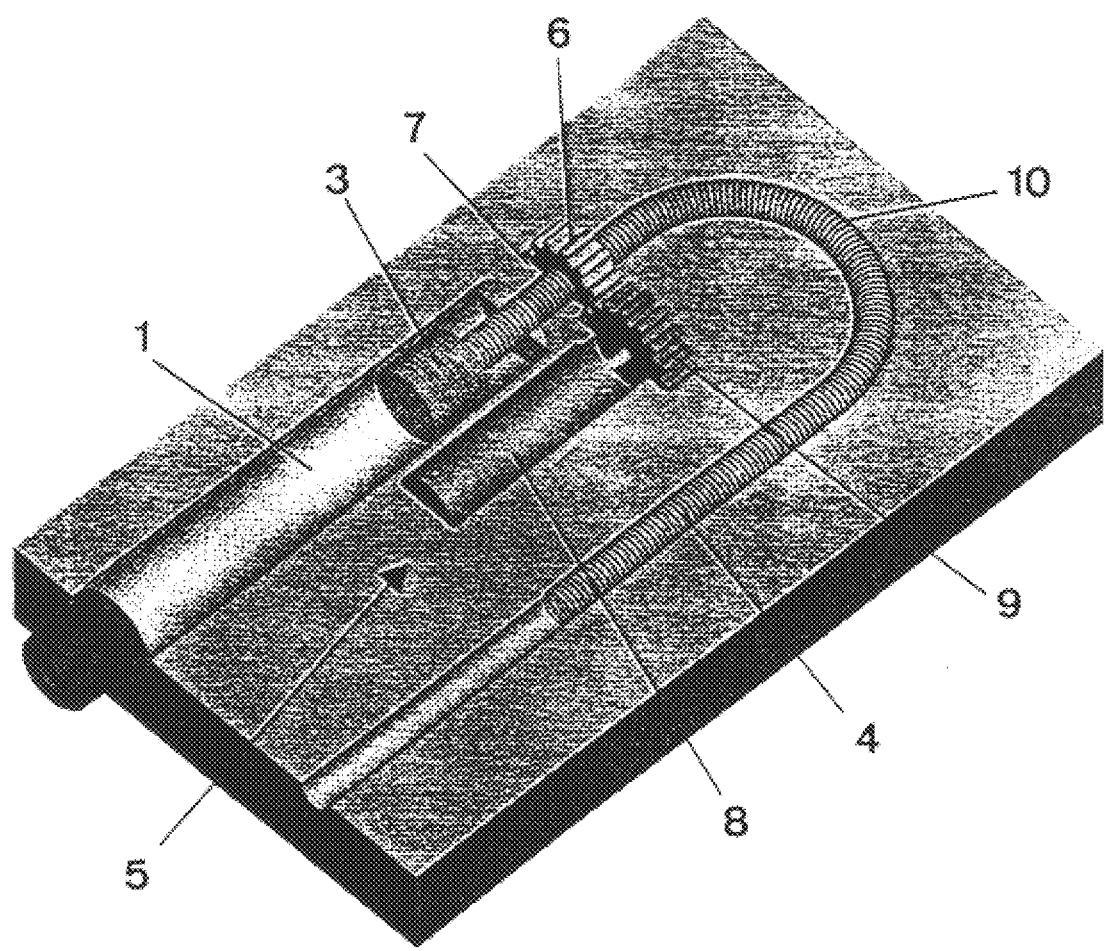
FIG. 3 Shows a perspective view of a displacement system having a flexible piston rod according to the invention.

A longitudinal spine 11 can be introduced into the spring simply by deforming the spring 4 on an out-turned area of each winding, which area covers an angle substantial smaller than 360 degrees. A permanently depression 11 of this type, making the spring non-circular, is schematically shown in FIG. 2. Applying a force, using an adequate tool, to the angular area could make a deformation or depression of the mentioned type, but such a deformation, restricted to a limited area of the spring, could also be made when coiling up the spring. Or it could be made by physically grinding away a part of the out-turned peripheral area of each winding.

If the spring 4 is of the extension type having a build-in initial tension, simply reducing or removing the initial tension on a longitudinal area of the spring can introduce a spine 11 into the spring 4, without physically changing the circular appearance of the spring 4. With the initial tension being removed or reduced in a longitudinal area, rotation of the bended spring 4 is made difficult due to the dislocated spine.

One way of removing the initial tension in an angular area of the helical spring 4 of the extension type is by applying a force to a limited angular part of the out-turned area of each winding, such a force can be applied by forcing the spring 4 over a relatively sharp edge, and thereby forcing a part of each of the backward pointing windings into a position eliminating the initial tension in that part of the winding. Together the part of each winding with no or reduced initial tension forms the longitudinal spine.

Some preferred embodiments have been shown in the foregoing, but it should be stressed that the invention is not limited to these, but may be embodied in other ways within the subject matter defined in the following claims.

What is claimed is:

1. A flexible piston rod for an injection device, having the form of a helical spring made up from a number of narrowly adjacent turns of windings providing an external thread for moving a piston forward inside a cartridge containing a liquid, said flexible piston rod transmitting a movement from a piston rod drive to a longitudinal displacement of said piston, said flexible piston rod having a distal end abutting said piston inside said cartridge and a proximal end being deflected away from the axis of said cartridge, said piston rod drive including a nut element having an internal thread engaging said external thread of said flexible piston rod and which nut element is locked against longitudinal displacement and forcedly rotated, characterized in that said flexible piston rod has means locking said flexible piston rod against rotation.

2. The flexible piston rod of claim 1, wherein said means locking said piston rod against rotation is a longitudinal spine located at the peripheral area of said helical spring forming the flexible piston rod.

3. The flexible piston rod of claim 2, wherein said helical spring has an initial tension and that the spine is a reduction or removal of the initial tension in a longitudinal area of said helical spring.

4. The flexible piston rod of claim 2, wherein the spine is a depression in the out-turned peripheral area of each winding covering an angular part being substantial smaller than 360 degrees.

5. The flexible piston rod of claim 2, wherein said spine is introduced in said spring by applying a momentarily force or a pressure over an area on the out-turned peripheral area of each winding.

6. The flexible piston rod of claim 5, wherein said momentarily force or said pressure is applied by forcing said flexible piston rod over a relatively sharp edge.

7. The flexible piston rod of claim 5, wherein the spine is introduced in said spring when the spring is being coiled.

8. The flexible piston rod of claim 2, wherein the spine is a physical removal of a part of the out-turned peripheral area of each winding covering an angular part being substantial smaller than 360 degrees.

9. The flexible piston rod of claim 8, wherein the removal of the material forming the part of the spring to be removed is done by grinding.

* * * * *